United States Patent [19]

Murata et al.

[11] Patent Number: 5,089,410

[45] Date of Patent: Feb. 18, 1992

[54] PROCESS FOR THE PRODUCTION OF BETACYANIN PIGMENTS

[75] Inventors: Yumiko Murata, Ageo; Masako Otsuka, Soka; Hiroshi Saimoto, Misato; Masao Kawashima, Warabi, all of Japan

[73] Assignee: Somar Corporation, Japan

[21] Appl. No.: 490,427

[22] Filed: Mar. 8, 1990

[30] Foreign Application Priority Data

Mar. 14, 1989 [JP] Japan .................................. 1-61470

[51] Int. Cl.$^5$ .............................................. C12N 5/00
[52] U.S. Cl. .................................. 435/240.45; 47/58; 435/240.4; 435/240.46; 435/240.48; 435/240.51; 435/240.54
[58] Field of Search ........... 435/240.4, 240.46, 240.48, 435/240.51, 240.54; 47/58

[56] References Cited

PUBLICATIONS

Jain et al., Chemical Abstracts, Abstract No. 144603k (1975).
Journal of Food Science, vol. 47, 1981, T. A. Weller, "Betalains in Beet Root Tissue Culture", pp. 162–163.

*Primary Examiner*—Douglas W. Robinson
*Assistant Examiner*—Jane A. Williams
*Attorney, Agent, or Firm*—Lorusso & Loud

[57] ABSTRACT

A biotechnological process for the production of betacyanin pigments is disclosed which comprises cultivating calli, induced from a plant which belongs to *Beta vulgaris* L. and which is capable of producing betacyanin pigments, in a liquid culture medium containing a reducing agent such as glutathione.

7 Claims, No Drawings

PROCESS FOR THE PRODUCTION OF BETACYANIN PIGMENTS

This invention relates generally to biotechnological production of betacyanin pigments and, more specifically, to a process for the production of betacyanin pigments by incubation, in a liquid culture medium, of callus induced from red beet.

Betacyanin pigments which are naturally produced by roots of red beet (a plant belonging to Beta vulgaris L.) have received much attention because of their utility as a red dye for foods. Betacyanin pigments are mainly composed of red to purple colored betacyanins and yellow to orange colored betaxanthins. The main ingredient of the betacyanins is betanin while that of betaxanthins is vulgaxanthin.

A variety of studies have been made on biotechnological production of betacyanin dyes, especially on cell culture of plant organs for the accumulation of betacyanin dyes (e.g. Journal of Food Science, 47, 162–163 (1981)). From the industrial standpoint, it is very important to improve the productivity of secondary metabolites in cell culture of plant organs. It has been found, however, when callus, induced from red beet tissues on a solid culture medium containing Murashige-Skoog culture medium, is incubated in a similar liquid culture medium for the growth of the cell thereof, the callus culture becomes gradually darkened and black colored and the desired betacyanin dyes are produced only in a small amount.

The present invention is aimed at the provision of an improved process capable of efficiently producing betacyanin dyes by cultivation of induced callus in a liquid culture medium. In accordance with the present invention there is provided a process for the production of betacyanin pigments, wherein calli induced from a plant which belongs to Beta vulgaris L. and which can produce betacyanin pigments are incubated in a liquid culture medium to produce betacyanin pigments, characterized in that said liquid culture medium contains a reducing agent.

The present invention will now be described in detail below.

Beta vulgaris L. involves various plants some of which can accumulate betacyanine dyes in roots thereof. Such betacyanin-producing plants are generally called red beet or table beet and are suitably used for the purpose of the present invention. Detroit dark red is a typical example of red beet. Sugar beet belonging to Beta vulgaris L. cannot produce betacyanin dyes in a large amount and is ill-suited for the purpose of the present invention.

The induction of red beet callus may be effected in any known manner. For example, a method disclosed in "SHOKUBUTSU SOSHIKI BAIYO (Plant Tissue Cultivation)", Takeuchi, M. et al, Asakura Shoten, Tokyo (1972); and "SHOKUBUTSU SAIBOU SOSHIKI BAIYO (Plant Cell Tissue Cultivation)", Harada, H. et al, Rikougakusha, Tokyo (1979) may be suitably used. The callus initially formed is generally a mixture of red colored, yellow colored and coloress cells. If red pigments are desired, it is advisable to collect red colored callus from the primary culture and to cultivate the collected callus. By repeating such collection and culture operations successively, there is obtainable callus rich in red pigments. The thus induced callus is added to a reducing agent-containing, liquid culture medium and the inoculum is incubated to accumulate red pigments.

The reducing agent is preferably a water-soluble organic or inorganic compound such as glutathione, ascorbic acid, isoascorbic acid, cysteine, sodium diethyldithiocarbamate, catechin, quercetin, sodium sulfite, sodium disulfite or sodium thiosulfate. Above all the use of glutathione, ascorbic acid, isoascorbic acid, cysteine or sodium diethyldithiocarbamate is particularly preferred. The concentration of the reducing agent in the liquid culture medium is preferably 0.1–100 mg/liter, more preferably 0.5–50 mg/liter.

Any liquid culture medium customarily used in cell culture of plant organisms may be used in the present invention. Illustrative of suitable liquid culture media are Murashige-Skoog medium, White medium, Linsmaier-Skoog medium, Gamborg B5 medium, Nitsch-Nitsch medium, Gantheret medium, Tulecke medium and Morel medium. Above all, the use of Gamborg B5 culture medium is particularly preferred. Compositions of typical culture media are given below:

| Ingredient | Concentration (mg/liter) | | |
|---|---|---|---|
| | Gamborg B5 medium | Murashige-Skoog medium | White medium |
| $KNO_3$ | 2,500 | 1,900 | 80 |
| $NH_4NO_3$ | — | 1,650 | — |
| $(NH_4)_2SO_4$ | 134 | — | — |
| $KH_2PO_4$ | — | 170 | — |
| $NaH_2PO_4 \cdot H_2O$ | 150 | — | 16.5 |
| $Ca(NO_3)_2 \cdot 4H_2O$ | — | — | 300 |
| $KCl$ | — | — | 65 |
| $CaCl_2 \cdot 2H_2O$ | 150 | 440 | — |
| $MgSO_4 \cdot 7H_2O$ | 250 | 370 | 720 |
| $NaSO_4$ | — | — | 200 |
| $Fe_2(SO_4)_3$ | — | — | 2.5 |
| $FeSO_4 \cdot 7H_2O$ | 27.8 | 27.8 | — |
| $Na_2$ EDTA | 37.3 | 37.3 | — |
| $MnSO_4 \cdot 4H_2O$ | — | 22.3 | 7 |
| $MnSO_4 \cdot H_2O$ | 10 | — | — |
| $ZnSO_4 \cdot 7H_2O$ | 2.0 | 8.6 | 3 |
| $H_3BO_3$ | 3.0 | 6.2 | 1.5 |
| $CuSO_4 \cdot 5H_2O$ | 0.025 | 0.025 | 0.001 |
| $Na_2MoO_2 \cdot 2H_2O$ | 0.25 | 0.25 | — |
| $MoO_3$ | — | — | 0.0001 |
| $KI$ | 0.75 | 0.83 | 0.75 |
| $CoCl_2 \cdot 6H_2O$ | 0.025 | 0.025 | — |
| myo-inositol | 100 | 100 | — |
| Thiamin hydrochloride | 10 | 0.1 | 0.1 |
| Pyridoxine hydrochloride | 1 | 0.5 | 0.1 |
| Nicotinic acid | 1 | 0.5 | 0.5 |
| Glycine | — | 2.0 | 3.0 |
| Sucrose | 20,000 | 30,000 | 20,000 |

As long as the basic characteristic of Gamborg B5 medium is maintained unchanged, it is possible to slightly change or modify the kind and/or amount of the above ingredients. Into the liquid culture medium, one or more phytohormones are generally incorporated. Illustrative of suitable phytohormones are auxins such as 1-naphthaleneacetic acid, indole-2-acetic acid, p-chlorophenoxyacetic acid, 2,4-dichlorophenoxyacetic acid, indole-3-butyric acid and derivatives thereof, and cytokinins such as 6-benzyladenine, kinetin and zeatin.

In the process according to the present invention, a pigment-containing red beet callus is sterilely added to a liquid culture medium containing a reducing agent and a phytohormone, and the resulting inoculum is incubated for the proliferation of the cells so as to accumulate the desired pigments.

The incubation is generally performed at a temperature of 10°-30° C., preferably 20°-30° C. for 1-3 weeks in the light or in the dark. Cultivation in the dark is preferred because the pigments tend to be decomposed when exposed to light. The incubation is generally continued until the logarithmic cell growth stage has been over and the stationary growth stage has been reached. Too long an incubation time is disadvantageous because of increased possibility of pigment decomposition.

By incorporation of the reducing agent into the liquid culture medium, the callus can grow intensively and effectively in a stable manner with the simultaneous accumulation of betacyanin pigments therein in a large amount. Mechanism of the prevention of discoloration attained by the addition of the reducing agent has not yet been clarified. Presumably, the reducing agent would serve to capture an inhibitor, such as active oxygen, which would advsersely affect growth of cells.

After incubation, the callus is separated from the liquid medium by, for example, filtration. Betacyanin pigments are then extracted from the callus by, for example, a known method adopted for the extraction of pigments from natural beet roots and disclosed, for example, in "TEN-NEN CHAKUSHOKURYO HANDOBBUK, Natural Coloring Matter Handbook", Tanimura, A. et al, Kourin, Tokyo (1979).

Similar to those obtained from natural beet roots, betacyanin pigments thus obtained according to the process of the present invention contain both red and yellow pigments. The high performance liquid chromatography and vissible light absorption spectroscopy have revealed that the pigments obtained in the present invention are mainly composed of betanin and bulgaxanthin. If desired, the red and yellow pigments may be separated from each other by, for example, liquid chromatography. If the callus containing red pigments only is used as a starting cultivation material, it is possible to produce only red pigments by the cultivation thereof.

The following examples will further illustrate the present invention. In the examples, percentages are by weight.

EXAMPLE 1

Induction of Callus

Seeds of Detroit dark red (commercially available from TAKII SEEDS AND SEEDLINGS INC.) were germinated and 7-day-old seedlings were sterilized with a 6% aqueous sodium hypochlomate solution for 10 minutes. The stems were cut into a length of several mm and placed on Murashige-Skoog agar medium (agar: 0.8%) modified with 1-naphthaleneacetic acid (5 mg/liter) and 6-benzyl adenine (0.1 mg/liter). These were then cultured in a dark condition at 25° C. for about 6 weeks to induce red callus. Especially red calli were selected and these were again cultured for about 6 weeks under the same conditions. Similar operations were repeated several times for generation to obtain a red callus sample stock which was used in the following examples.

Cultivation in Liquid Culture Medium

Murashige-Skoog culture medium (40 ml) modified with 1-naphthaleneacetic acid (5 mg/liter) and 6-benzyladenine (0.1 mg/liter) and glutathione (3 mg/liter) were charged into a 100 ml Erlenmeyer flask, to which was added sterilely the above callus sample (0.8 g). The inoculum was incubated at 25° C. in the dark for 2 weeks with stirring at 100 r.p.m. Observation of the resulting callus culture revealed a small amount of darkened, discolored callus with the remainder thereof being red. The fresh weight (cell yield) was 5.3 g.

EXAMPLE 2

Callus cultivation was conducted in the same manner as described in Example 1 except that White culture medium was used in lieu of Murashige-Skoog culture medium. Observation of the resulting callus culture revealed a small amount of darkened, discolored callus with the remainder thereof being red. The fresh weight was 6.4 g.

EXAMPLE 3

Callus cultivation was conducted in the same manner as described in Example 1 except that Gamborg B5 culture medium was used in lieu of Murashige-Skoog culture medium. Observation of the resulting callus culture revealed that almost all calli remained red. The fresh weight was 10.5 g.

EXAMPLE 4

Callus cultivation was conducted in the same manner as described in Example 3 except that the concentration of glutathione was increased to 10 mg/liter. Observation of the resulting callus culture revealed that almost all calli remained red. The fresh weight was 11.2 g.

COMPARATIVE EXAMPLE 1

Callus cultivation was conducted in the same manner as described in Example 1 except that no glutathione was used. After 1 week from the commencement of the incubation, the callus culture was disclored and darkened. The fresh weight was 1.3 g.

COMPARATIVE EXAMPLE 2

Callus cultivation was conducted in the same manner as described in Example 2 except that no glutathione was used. After 1 week from the commencement of the incubation, the callus culture was disclored and darkened. The fresh weight was 1.6 g.

COMPARATIVE EXAMPLE 3

Callus cultivation was conducted in the same manner as described in Example 3 except that no glutathione was used. After 1 week from the commencement of the incubation, the callus culture was disclored and darkened. The fresh weight was 1.4 g.

EXAMPLE 5

Callus cultivation was conducted in the same manner as described in Example 3 except that ascorbic acid was substituted for glutathione. Observation of the resulting callus culture revealed that almost all calli remained red. The fresh weight was 8.6 g.

EXAMPLE 6

Callus cultivation was conducted in the same manner as described in Example 4 except that ascorbic acid was substituted for glutathione. Observation of the resulting callus culture revealed that almost all calli remained red. The fresh weight was 8.8 g.

EXAMPLE 7

Callus cultivation was conducted in the same manner as described in Example 3 except that cystein was substituted for glutathione. Observation of the resulting callus culture revealed that almost all calli remained red. The fresh weight was 9.0 g.

EXAMPLE 8

Callus cultivation was conducted in the same manner as described in Example 3 except that sodium sulfite was substituted for glutathione. Observation of the resulting callus culture revealed a small amount of darkened, discolored callus with the remainder thereof being red. The fresh weight was 6.2 g.

EXAMPLE 9

The callus culture obtained in Example 8 was combined with 50 ml of water and the mixture was homogenized with Polytron Homogenize (Kinematica GmbH) and then filtered to obtain a red pigment-cotaining aqueous solution. The solution was lyophilized with Neocool Freeze Dryer (Yamato Scientific Co., Ltd.) to recover red pigment powder.

What is claimed is:

1. A process for the production of betacyanin pigments, wherein calli induced from a plant which belong to *Beta vulgaris* L. and which is capable of producing betacyanin pigments are incubated in a liquid culture medium to produce betacyanin pigments, characterized in that said liquid culture medium contains a reducing agent selected from the group consisting of glutathione, ascorbic acid, isoascorbic acid, cysteine, diethyl dithiocarbonate, catechin, quercetin, sodium sulfite, sodium metabisulfite and sodium thiosulfite.

2. A process as claimed in claim 1, wherein the concentration of said reducing agent in said liquid culture medium is 0.1-100 mg/liter.

3. A process as claimed in claim 1, wherein said liquid culture medium is Murashige-Skoog medium, White medium, Linsmaier-Skoog medium, Gamborg B5 medium, Nitsch-Nitsch medium, Gantheret medium, Tulecke medium and Morel medium.

4. A process as claimed in claim 1, wherein said liquid culture medium is Gamborg B5 medium and said reducing agent is selected from the group consisting of glutathione, ascorbic acid, isoascorbic acid, cystein and diethyl dithiocarbonate.

5. A process as claimed in claim 1, wherein said liquid culture medium further contains a phytohormone.

6. A process as claimed in claim 5, wherein said hormone is selected from the group consisting of auxins and cytokinins.

7. A process for the production of betacyanin pigments in accordance with claim 1, wherein said reducing agent is selected from the group consisting of glutathione, cysteine, diethyl dithiocarbonate, catechin, quercetin, sodium sulfite, sodium metabisulfite and sodium thiosulfite.

* * * * *